US005760407A

United States Patent [19]

Margosiak et al.

[11] Patent Number: 5,760,407
[45] Date of Patent: Jun. 2, 1998

[54] DEVICE FOR THE IDENTIFICATION OF ACNE, MICROCOMEDONES, AND BACTERIA ON HUMAN SKIN

[75] Inventors: Marion Louise Margosiak, Mahwah; Helen Elizabeth Knaggs, Fairview, both of N.J.; Michael Paul Aronson, West Nyack, N.Y.

[73] Assignee: Elizabeth Arden Co., Division of Conopco, Inc., New York, N.Y.

[21] Appl. No.: 903,967

[22] Filed: Jul. 31, 1997

Related U.S. Application Data

[63] Continuation of Ser. No. 576,526, Dec. 21, 1995, abandoned.

[51] Int. Cl.⁶ ............................................. G01N 21/64
[52] U.S. Cl. .................................. 250/461.2; 250/461.1
[58] Field of Search .............................. 250/461.1, 461.2; 600/476

[56] References Cited

U.S. PATENT DOCUMENTS

| | | |
|---|---|---|
| 3,992,631 | 11/1976 | Harte . |
| 4,056,724 | 11/1977 | Harte . |
| 4,071,020 | 1/1978 | Pugliese ................... 250/461.2 X |
| 4,127,773 | 11/1978 | West ........................... 250/461.1 |
| 4,133,639 | 1/1979 | Harte . |
| 4,144,452 | 3/1979 | Harte . |
| 4,236,082 | 11/1980 | Butler ........................... 250/461.1 |
| 4,395,126 | 7/1983 | Kramer ...................... 250/461.1 X |
| 4,800,282 | 1/1989 | Nishimura ..................... 250/461.1 |
| 4,841,156 | 6/1989 | May et al. ..................... 250/461.1 |
| 4,894,547 | 1/1990 | Leffell et al. ................ 250/461.1 X |
| 5,034,615 | 7/1991 | Rios et al. .................... 250/461.1 |
| 5,343,536 | 8/1994 | Groh .............................. 382/133 |
| 5,363,854 | 11/1994 | Martens et al. . |
| 5,371,624 | 12/1994 | Nagano et al. . |
| 5,450,857 | 9/1995 | Garfield et al. . |

FOREIGN PATENT DOCUMENTS

| | | |
|---|---|---|
| 478 026 | 4/1992 | European Pat. Off. . |
| 4120688 | 1/1993 | Germany . |
| WO 93/13403 | 7/1993 | WIPO . |
| WO 94/16622 | 8/1994 | WIPO . |

OTHER PUBLICATIONS

European Search Report in European Patent Application No. 96308054.4.
Derwent Abstract of DE 4120688 published Jan. 14, 1993.
Sauermann et al., "Analysis of Facial Comedos by Porphyrin Fluorescence and Image Analysis", J. Toxicol.—*Cut & Ocular Toxicol.*, vol. 8, No. 4, (1989–1990), pp. 369–385.
Sauermann et al., "A Novel Fluorimetric Method to Investigate Sebaceous Glands in Humans", *Non–Invasive Methods for the Quantification of Skin Functions*, Peter J. Frosch and A. Kligman ed., Springer–Verlag, 1993, pp. 252–271.
Czernielewski et al., "Oral Treatment of Acne Vulgaris and Oil Acne with Tetracycline", *Dermatologica*, (1982) 165:pp. 62–65.
Costello et al., "Fluorescence with the Wood Filter as an Aid in Dermatologic Diagnosis", *New York State J. Med.*, vol. 44, (1944) pp. 1778–1784.
Lucchina et al., "Fluorescence Photography in the Evaluation of Acne", Journal of the American Academy of Dermatology, vol. 35, No. 1, pp. 58–63 (1996).

*Primary Examiner*—Edward J. Glick
*Attorney, Agent, or Firm*—Rimma Mitelman

[57] ABSTRACT

The invention relates to a device and a method for the identification of fluorescing follicles that can be follicular impactions and/or microcomedones (clinically non-evident acne lesions), and/or comedones (clinically evident acne lesions) and/or bacteria on the face or other skin surface area. The inventive device allows the detection of both types of follicular fluorescence (yellow/green and orange/red). For safety reasons, to prevent skin burns and erythema, the filter on the ultraviolet light source removes substantially all the harmful UVB radiation (280–320 nm wavelength range). The filter used in conjunction with the detection means removes reflected and scattered light emanating from the subject's skin surface, thus increasing the sensitivity and discretion of the technique and making fluorescence detection easier and clearer.

4 Claims, 1 Drawing Sheet

DEVICE FOR THE IDENTIFICATION OF ACNE, MICROCOMEDONES, AND BACTERIA ON HUMAN SKIN

This is a continuation application of Ser. No. 08/576,526, filed Dec. 21, 1995, now abandoned.

FIELD OF THE INVENTION

The invention relates to a device and a method for the identification of fluorescing follicles that can be follicular impactions and/or microcomedones (clinically non-evident acne lesions), and/or comedones (clinically evident acne lesions) and/or bacteria on the face or other skin surface area.

BACKGROUND OF THE INVENTION

Acne affects pilosebaceous follicles within the skin. At least six types of acne are known, e.g., acne vulgaris. Four processes are thought to be involved in the pathogenesis of acne: sebum production, ductal hypercornification, bacterial colonization of a pilosebaceous follicle and inflammation. Clinically, acne is characterized by the appearance of comedones (non-inflamed lesions) and inflamed lesions (papules and pustules). Ductal hypercornification is caused by the increased proliferation of the basal ductal keratinocytes and increased adhesion between the corneocytes of the duct wall. This leads to a build-up of corneocytes in the duct lumen which becomes mixed with sebum produced by the sebaceous gland, resulting in follicular impactions. If the correct conditions prevail, the follicular impactions can develop into comedones. Microcomedones represent an intermediate stage in the development of acne. Comedones are clinically evident, but follicular impactions and microcomedones are not. Once the comedones, or follicular impactions, or microcomedones are formed, the duct lumen offers a suitable microenvironment for colonization by bacteria. The bacteria thought to be responsible for acne is P. acnes.

It is desirable to be able to detect follicular impactions and microcomedones in order to provide a timely skin treatment and to prevent the appearance of comedones. It is also desirable to distinguish between bacteria-populated and non-bacterial follicles, because the treatment may differ depending on the presence or absence of the bacteria within the follicle.

The bacteria produce porphyrins which upon excitation, fluoresce orange-red. On a cyanoacrylate gel biopsy, the follicular impactions have been shown to possess a yellow/green fluorescence.

Wood's light, a longwave UV light, has been used to visualize pigmentation disorders, as a diagnostic tool for skin diseases such as erythrasma, tinea capitis, bacterial infections, hand dermatosis, and psoriasis, etc. Wood's light has also been used to identify follicular casts in-vitro obtained by cyanoacrylate gel biopsy method, to investigate sebaceous glands in humans and to analyze facial comedones by porphyrin fluorescence. Modified Wood's light (i.e., its tube coated with polymer/organic UV absorber) is also used for suntanning.

Sauermann et al, disclosed in "Analysis of Facial Comedos by Porphyrin Fluorescence and Image Analysis" in J. Toxicol.—Cut. & Ocular Toxicol., 8 (4), pp. 369–385, 1990, an experimental set-up in which skin sites were irradiated with either UVA light (max 350 nm) or monochromatic light. Reflected light was avoided by bandpass filters (lambda (>50% transmission)>560 nm). It is unclear how large the bandpass was. The author mentions yellow/green and orange fluorescence. The author's theory about what is responsible for each color of fluorescence is confusing. The abstract mentions that this paper will investigate the comedogenicity of products by measuring the yellow spots. In the visual observations, intense yellow/green or orange fluorescence is mentioned and correlated to "special sebaceous glands of different size." The images were transformed into binary images and then into histograms to yield the parameters of count and individual size. The title of the histogram is "Density of facial porphyrin-fluorescence." From the information gained here, it appears that the author is correlating the yellow spots with porphyrin fluorescence. The detection was performed by a sensitive light-amplifying camera without any cut-off filter.

The second paper by Sauermann et al. entitled "A Novel Fluorimetric Method to Investigate Sebaceous Glands in Humans" in "Non-Invasive Methods for the Quantification of Skin Functions", Peter J. Frosch and A. Kligman ed., Springer-Verlag, 1993, investigated the comedogenicity of raw materials and consumer products. The author assumed that fluorescence intensity is strongly related to the population density of P. acnes and porphyrin content at the skin surface. The disclosed instrument included a 610 nm cutoff filter in front of the camera thus removing the yellow/green fluorescence (500–580 nm) from the images. The author related the orange/red fluorescence to comedone activity.

The devices employed by Sauermann either did not employ cut-off filters for both the light source and for the detection or employ cut-off filters which differed from those employed in the device of the present invention. Furthermore, Sauermann et al. did not disclose or suggest that microcomedones/comedones not populated by bacteria and those that are populated by bacteria correspond to two different fluorescence colors. Furthermore, the Sauermann devices were not portable.

By contrast, the device according to the present invention employs filters for both the light source and the detection means. By virtue of the inclusion of these filters, the inventive device prevents sunburn from the light source and allows clear differentiation between the bacterial and non-bacterial follicular impactions. Additionally, in a preferred embodiment of the invention, the device is portable.

SUMMARY OF THE INVENTION

The present invention includes, in part, a safe device for detecting bacteria, follicular impactions and/or microcomedones, and comedones on human skin. The inventive device contains a light source and a fluorescence detection means, which are both equipped with either a single filter or a plurality of filters. In the first embodiment of the invention, the light source is an ultraviolet light in conjunction with a filter which removes substantially all light below 350 nm, in order to avoid sunburn. In the first embodiment of the invention, the filter is defined as having less than 10% transmission of the UVB region and greater than 50% transmission at 400 nm and above.

In the second embodiment of the invention, the light source is a white light in conjunction with a bandpass filter for the light source which allows a broadband of UVA light (320 to 400 nm) to pass.

In both embodiments of the invention, the fluorescence detection means is equipped with a single filter or a plurality of filters which remove substantially all light below 450 nm.

In the preferred embodiment of the invention, the device is portable—both UV source and white source including detection means can be portable.

The inventive device allows the detection of both types of follicular fluorescence (yellow/green and orange/red). For safety reasons, to prevent skin burns and erythema, the filter on the ultraviolet light source removes substantially all the harmful UVB radiation (280–320 nm wavelength range). The filter used in conjunction with the detection means removes reflected and scattered light emanating from the subject's skin surface, thus increasing the sensitivity and discretion of the technique and making fluorescence detection easier and clearer.

Yellow/green fluorescence indicates the presence of follicular impactions, including comedones and microcomedones. Orange/red fluorescence indicates the presence of P. acnes bacteria living within and on the surface of the follicular impactions or the comedones. Thus, the inventive device allows the detection of follicular impactions and/or microcomedones, which are not clinically evident under normal lighting. The device also improves the visualization of comedones (especially small lesions), which are clinically evident under normal lighting conditions. Furthermore, the inventive device makes it possible to distinguish between bacteria-populated and non-bacterial follicular impactions and comedones.

The device may, for example, be advantageously used by dermatologists as a research tool. The device may also be employed at cosmetic counters to diagnose or identify the presence of follicular impactions and microcomedones and to determine whether the follicular impactions, microcomedones and comedones are populated with bacteria or not, which in turn determines the best treatment for a particular subject.

DETAILED DESCRIPTION OF THE INVENTION

The inventive device includes two essential parts: a light source and a detection means, both of which are equipped with light filters.

Figure 1:
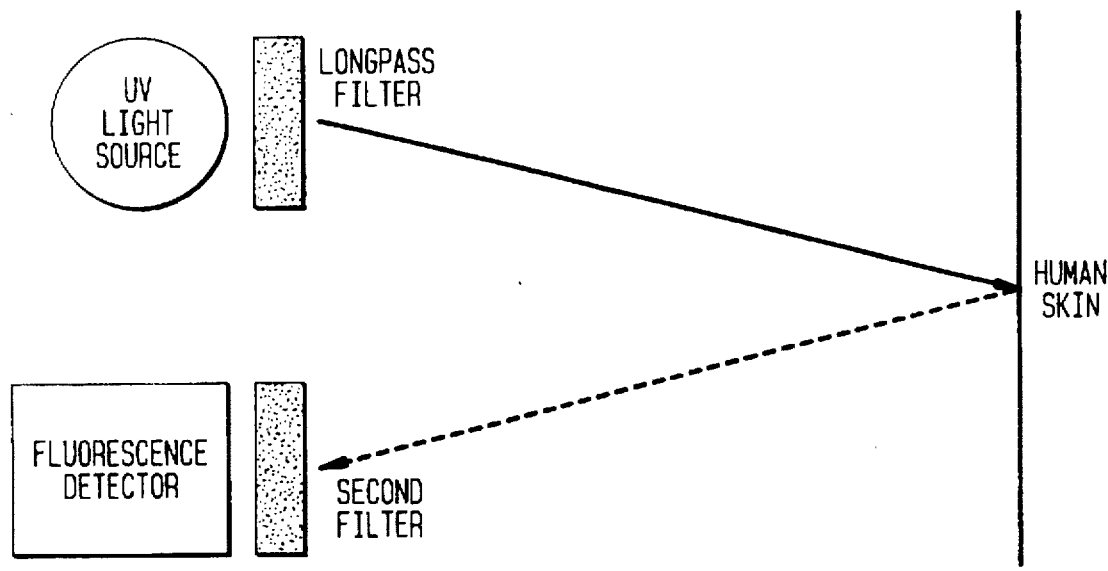
FIGS. 1 and 2 schematically illustrate different embodiments of the invention.

In the first embodiment of the invention, as shown in FIG. 1, the light source is an ultraviolet light in conjunction with a longpass filter which removes substantially all light below 350 nm. In the first embodiment of the invention, the filter is defined as having less than 10% transmission of the UVB region and greater than 50% transmission at 400 nm and above. The longpass filter is preferred to remove substantially all of the harmful UVB region (280–320 nm) and pass substantially all light above 350 nm. This higher wavelength is required to excite the fluorescence of follicular contents of interest.

The term "longpass" when used to define filter for the UV light source of the inventive device means that a filter allows more than 50% transmission of lightwaves that have a wavelength above the specified wavelength of the filter.

Figure 2:
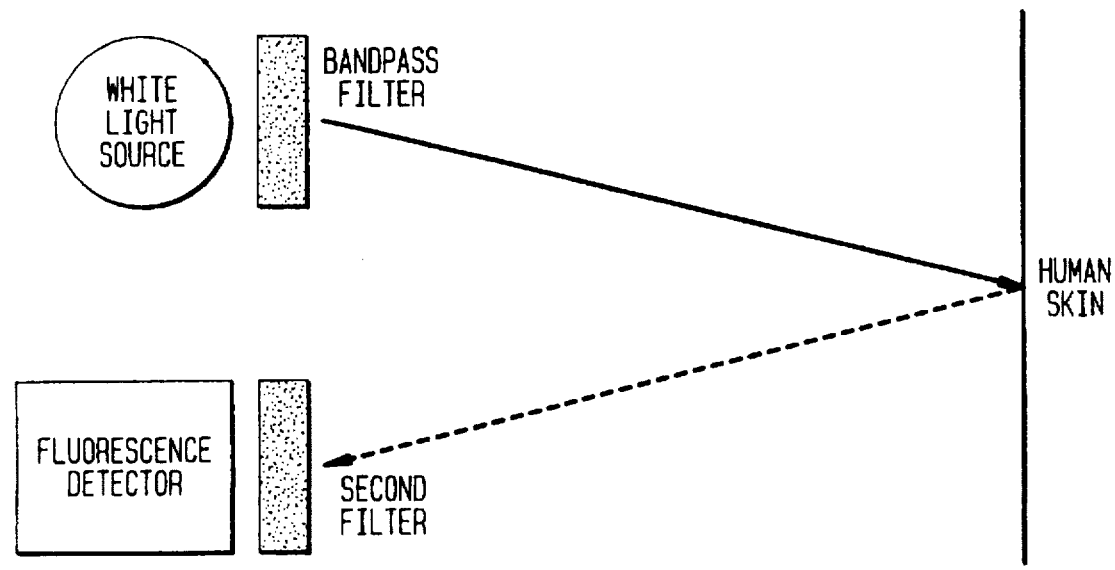

In the second embodiment of the invention, as shown in FIG. 2, the light source is a white light in conjunction with a broadband bandpass filter which allows a broadband of UVA light (320 to 400 nm) to pass. The preferred bandpass range is 340–400 nm. The most preferred bandpass range is 360–400 nm.

The term "bandpass" when used to define a filter for the white light source of the inventive device means a narrowband (unless specified) interference filter that allows 50% transmission or greater of light at wavelengths at the full width at half maximum around the specified wavelength of the filter.

In both embodiments of the invention the light source may be either continuous or pulsed. The light source and the filter therefore must be either connected or in the close proximity to each other such that no light from the light source is emitted that did not pass through the filter.

In both embodiments of the invention, the fluorescence detection means is equipped with at least a single filter which removes substantially all light below 450 nm, preferably substantially all light below 480 nm, and most preferably substantially all light below 500 nm. Thus, the device removes scattered and reflected light from the light source off the subject's skin surface.

The filter for the detection means is employed in the present invention to ease the detection of the fluorescence and to make it possible to differentiate between bacteria-populated and non-bacterial follicular impactions, microcomedones and comedones.

The filter for the detection means may be a single filter or a plurality of filters. A plurality of filters may be employed to pinpoint a particular wavelength range, as long as the wavelength range is at least from 480 nm to 680 nm, i.e., the detection device must be able to detect light within the 500–580 nm wavelength range (yellow/green fluorescence) and within the 580–680 nm wavelength range (orange/red fluorescence).

Suitable filters for the detection means include but are not limited to:

i) a longpass filter to detect both yellow/green and orange/red fluorescence;

ii) a longpass filter and a shortpass filter to detect yellow/green fluorescence;

iii) a longpass filter and a shortpass filter to detect orange/red fluorescence;

iv) a bandpass filter to detect yellow/green fluorescence;

v) a bandpass filter to detect orange/red fluorescence;

vi) a longpass filter to detect orange/red fluorescence; and vii) optical tunable filter as described in I. C. CHANG, Acousto optic devices and applications, pp. 12.1–12.54. In: Handbook of Optics, Devices, Measurement and Properties. Vol 2. Editor: Micheal Bass. Published by MacGraw Hill Inc, 1995.

The longpass filter for the fluorescence detection means in i) and ii) is defined as lambda >50% transmission at 450 nm and above. The shortpass filter in ii) is defined as lambda >50% transmission at 600 nm and below. The longpass filter in iii) and vi) is defined as lambda >50% transmission at 600 nm and above. The shortpass filter in iii) is defined as lambda >50% transmission at 700 nm and below.

The term "bandpass" as used for the fluorescence detection means is defined as a broadband interference filter that allows >50% transmission of wavelengths at the full width at half maximum around the specified wavelength of the filter. The bandpass filter in iv) is defined to cover the 480–580 nm wavelength range. The bandpass filter in vi) is defined to cover the 580–680 nm wavelength range.

Suitable detection means include but are not limited to eyeglasses or eyeglass frames, a film emulsion camera, or a Charged-Coupled Device (CCD) camera (normal, intensified or amplified).

The detection means and the filter therefore must be either connected or in close proximity to each other, so that substantially all light from the subject's skin surface passes through the filter.

A single filter or a system of multiple filters is suitable for use in the inventive device, as long as the filter or filters for the light source allow suitable intensity from the light source to excite fluorophores on the subject's skin surface. Also, as long as the filter or filters for the detection means allows sufficient fluorescence intensity in the 480–680 nm wavelength range to reach the detection means.

In the preferred embodiment of the invention, the device is portable. The device must be capable of being carried or moved without being bulky in size and consist of a bearable weight.

The invention also includes a method for identifying the presence of follicular impactions, microcomedones and comedones on human skin, wherein the skin is illuminated with the light from the light source, causing the fluorescence of follicular impactions, ductal hypercornification, microcomedones, comedones and porphyrins produced by Propionibacterium acnes bacteria. Follicular impactions including microcomedones and comedones fluoresce in the yellow/green portion of the spectrum (480–580 nm) and the porphyrins produced by Propionibacterium acnes bacteria fluoresces in the red portion of the spectrum (580–680 nm). The fluorescence is detected visually with eyeglasses or any other detection system. The detection system is modified with the aid of a filter removing scattered and/or reflected light off the subject's skin surface.

EXAMPLE 1

This example demonstrates the inventive device according to the first embodiment of the invention.

The subject, wearing ultraviolet protective eye shields ("PEEPERS", #C015-2, California SunCare, Inc.), sat in a chair. The Wood's Lamp (UVP Longwave Hand Lamp with Handle, Model #UVL-56, 6 watt Blak-Ray longwave ultraviolet tube, 600 microwatts at 365 nm at a 6 inch distance, measured energy at 6 inches is $2.23 \times 10^{-4}$ J/s/cm$^2$.) With attached WG345 (Oriel Corp.) longpass filter was switched to the "on" position and held six inches from the subject's skin surface. The investigator wore eyeglasses containing two GG435 (Oriel Corp.) longpass filters (one for each eye). These filters in the investigator's eyeglasses removed any scattered or reflected light from the light source and the subject's skin surface making the intrinsic fluorescence brighter and clearer. The investigator was able to observe small and large yellow/green spots on a low intensity dull bluish skin surface. Also seen were small orange/red spots on the skin surface. It was always possible to distinguish between yellow/green and orange/red fluorescence even if they appeared at a single spot.

In the above example, the detection device was the human eye with filters. When the detection device was used without the aid of longpass filters, the investigator would observe only large fluorescing spots on a high intensity blue background. By virtue of employing a filter on the detection means (human eyes in this example), it was possible to see even small spots and it was possible to differentiate clearly between the two types of fluorescence even if they were superimposed.

COMPARATIVE EXAMPLE 2

The subject wearing ultraviolet protective eye shields ("PEEPERS", #C015-2, California SunCare, Inc.) sat in a chair. Monochromatic light (385+/−8 nm), which is not within the scope of the present invention, from a fiber optic assembly attached to an ISS.K2 Fluorometer was shown over the facial skin surface approximately one inch from the skin surface. The detection method for fluorescence was the human eye. Microcomedones and/or follicular impactions, comedones and bacterial populated follicles were identified. The skin background was observed as a bluish color which was a direct result of scattered or reflected light from the light source off the skin surface into the detector. Microcomedones and/or follicular impactions were observed through the blue reflected light as yellow/green fluorescing spots on the skin surface. Comedones were observed fluorescing yellow/green but were sometimes larger in size than the microcomedones. Some microcomedones and/or follicular impactions and comedones were also observed to contain orange/red fluorescence within and on the surface of the follicle. Orange/red fluorescence was also observed within and on the surface of the follicle in the absence of the yellow/green fluorescence.

However, with this method, only a small skin surface area was illuminated, the light intensity was low, and, in the absence of a filter blocking system for the human eye, the blue light was not removed and the fluorescence was dull and unclear. Furthermore, although the human eye can distinguish the yellow/green and orange/red fluorescence from the intense blue background because of human logic, conventional cameras cannot separate the colors without the aid of filters.

EXAMPLE 3

This example demonstrates the inventive device according to the second embodiment of the invention.

The subject with ultraviolet protective eye shields ("PEEPERS", #C015-2, California SunCare, Inc.) is positioned into a stereotactic face device (a head brace which holds the head in one position providing there is a constant pressure on the brace from the subject) (Canfield Scientific Inc.). The light source was full spectrum light from UVA to infrared (Balcar Super A Package, Calumet Photographic, Inc.). The light source was covered completely with a bandpass filter that emitted a distribution of UVA radiation peaking at 365 nm (UV black light filter, #20316, Calumet Photographic, Inc.). The detection source was a film emulsion camera (Nikon F3HP 35 mm, 105 mm F2.8 Micro-Nikkor lens, Nikon MD-4 motor drive and a Nikon MF-14 data back) containing color film (Kodak Ektachrome Elite 400, 135–36). The lens of the camera was fitted with a GG455 longpass filter (lambda >50% at 450 nm) (Oriel Corp.) within a Nikon Gelatin Filter Holder AF-1 with a UR-2 special filter holder accessory to remove reflected light from the light source off the skin surface. The camera was focused to an area on the skin surface with a reproduction ration of 1:1 and the picture was taken in a darkened room. The images appeared to have a low intensity dull bluish background with small and large yellow/green spots within follicles. Some yellow/green follicles also contained small orange/red fluorescent spots. Also observed were small orange/red fluorescent spots alone within and on the surface of the follicle.

1. Observations without longpass filter on the lens: Images were observed to be a high intensity blue color. The low intensity fluorescence is not detectable within the blue background. Facial features can be distinguished.

2. Observations with both a shortpass and longpass or a bandpass filter on the lens to observe yellow/green fluorescence: The longpass filter for the camera is defined as lambda >50% transmission at 450 nm and above. The shortpass filter is defined as lambda >50% transmission at 600 nm and below. The shortpass and longpass filter together make a bandpass of 75 nm at full width at half maximum wavelength. Images are observed to have a low intensity, dull greenish background with more intense yellow/green spots.

3. Observations with a longpass filter on the lens to observe orange/red fluorescence: The longpass filter for the camera is defined as lambda >50% transmission at 600 nm and above. Images are observed to have a low intensity, dull red background with more intense orange/red spots.

EXAMPLE 4

The subject with ultraviolet protective eye shields ("PEEPERS", #C015-2, California SunCare, Inc.) was positioned into a stereotactic face device (a head brace which holds the head in one position providing there is a constant pressure on the brace from the subject) (Canfield Scientific Inc.). The lamp source was a 300 watt ozone free Xenon lamp enclosed within a 500 watt universal arc lamp housing with a built-in ignition and a F/1.0 condenser (L1) used to collimate the beam (Oriel Corp.#66084, #6258 and #66011). The lamp source was powered by a 200–500 watt Mercury (Xenon) power supply (Oriel Corp. #68811). Connected to the lamp condenser was a water filter (Oriel Corp. #61945) connected to a recirculating cooler (Oriel Corp. #60200) with a flow rate of greater than 21/min. This was used to remove heat generated from the light source. The recirculating cooler used a water to air heat exchanger to remove heat in an unregulated manner. The liquid water filter used a fused silica window to pass the 250–950 nm range and absorb the NIR. After the water filter, the light passed through a manual filter holder (Oriel Corp. #62020) containing an infrared blocking filter (F1) and a bandpass filter (F2). The infrared blocking filter (F1, Oriel Corp. #59060) had a 0.1% transmittance and further reduced the infrared radiation to pass a broad band from 365 nm to 680 nm. The bandpass filter, F2 (Oriel Corp. #59805) had a full width half maximum (FWHM) equal to 80 nm from 340–420 nm with a maximum transmission of 80%. Next in the series was a fiber optic focusing assembly (Oriel Corp. #77800) that contained a F/2 fused silica focusing lens which focused collimated light onto the face of a fiber or bundle and a built-in shutter so one could close off the beam without shutting down the light source. The UV-VIS liquid light guide had a spectral range of 250–700 nm (Oriel Corp. #77557). The liquid light guide was then connected to a collimating beam probe (L2) with shutter (Oriel Corp. #77652) and a fiber optic rod mount (Oriel Corp. #77612). To further reduce the band of light from the liquid light guide, a bandpass filter (F3) (Oriel Corp. #57510) was attached to the fiber optic rod mount. The filter had a FWHM of 50 nm from 372.5–422.5 with a maximum transmission of 61%. These filters provided an estimated excitation light bandwidth of 34 nm (FWHM) from 373–407 nm. A dichroic mirror (Omega Optical, #425DCLP) placed in front of the microscope objective was used to provide uniform illumination to the skin surface. The dichroic mirror had a 50% transition point at 425 nm where shorter wavelengths are reflected and longer wavelengths are passed to the microscope objective.

The Infinivar Video Inspection Microscope, "InfiniVar", has the capability to continuously focus from infinity to 10 mm working distance (Infinity Photo Optical Co.). The objective was a 10 element/6 group 'optics module' that has a variable power of 0.2× to 8× at a 145 to 10 mm working distance. The microscope, at a working distance of 145 mm and 10 mm, had a numerical aperture value of 0.015 and 0.25 respectively. The magnification was 6× to 241× rated for a 19" monitor and 1" camera, with a magnification variation of 40 to 1 ratio. The measured maximum magnification at a 10 mm working distance was 232×.

The skin auto-fluorescence and a small fraction of reflected excitation light passed through the dichroic mirror into the microscope objective. In order to remove the excitation light, a longpass filter (Oriel Corp. #52095) with a cut-on wavelength of 470 nm was placed inside the microscope (F4). This filter efficiently removed the excitation light from the sensitive intensified CCD camera. This particular filter was chosen because longpass filters below 470 nm pass some excitation light and result in a slight amount of noise, while longpass filters above 470 nm removed more skin auto-fluorescence.

The camera chosen to detect very low-light levels of fluorescence from the subject was a black and white extended ISIS Intensified CCD camera (Photonic Science Ltd.). In the extended ISIS camera, the intensifier was a custom built hybrid with a S20 photocathode for peak response in the 400–500 nm region and lower background noise. The intensifier was optimized at 500 nm with a maximum sensitivity of 60 mA/W corresponding to 12% quantum efficiency. The image was transferred from the intensifier to the image sensor using coherent fiber optic components which is at least an order of magnitude more efficient than lens coupling. The limiting resolution was 620 TV/lines per picture width with an input image size of 18 mm diagonal rectangle with an aspect ratio of 3:4 (standard video format). The CCD sensor utilizes a line transfer device with 753 active horizontal pixels per line and 576 vertical lines.

The camera and microscope was focused to an area on the skin surface, the shutter was opened to allow ultraviolet illumination and the picture was taken in a darkened room. Digitized images were acquired and saved with a 2:1 ratio and a 30× magnification. After image acquisition, the shutter was closed. Images showed a dark skin background with bright white spots that are indicative of the yellow/green fluorescence of follicular impactions and the orange/red fluorescence of porphyrins produced by P. acnes.

EXAMPLE 5

The device of Example 4 is modified with an AOTF filter (Accoustic Optical Tuning Filter) in front of the illumination source and before the CCD camera. The AOTF filter allows the investigator to control the specified wavelengths, the width of a bandpass and the wavelength of a shortpass or longpass filter.

What is claimed is:

1. A safe device for detecting non-bacterial follicular impactions, microcomedones and comedones on human skin, the device comprising:

(a) an ultraviolet light source in conjunction with a longpass filter which removes substantially all light below 350 nm for illuminating said skin;

(b) a fluorescence detection means in conjunction with a filter or a plurality of filters which pass light in the wavelength range 480–580 nm, such that the detection means is able to detect fluorescent light from said skin within the 500–580 nm wavelength range (yellow/green fluorescence).

2. A safe device for detecting bacterial follicular impactions, microcomedones and comedones on human skin, the device comprising:
   (a) an ultraviolet light source in conjunction with a longpass filter which removes substantially all light below 350 nm for illuminating said skin;
   (b) a fluorescence detection means in conjunction with a filter or a plurality of filters which pass light in the wavelength range 580–680 nm, such that the detection means is able to detect fluorescent light from said skin within the 580–680 nm wavelength range (orange/red fluorescence).

3. A method of distinguishing between bacterial (orange/red fluorescence) and non-bacterial (yellow/green fluorescence) follicular impactions, microcomedones and comedones on human skin, the method comprising:
   (a) illuminating the skin with light from an ultraviolet light source in conjunction with a longpass filter which removes substantially all light below 350 nm to cause fluorescence of the skin;
   (b) detecting yellow/green fluorescence and orange/red fluorescence by using a detection means in conjunction with a filter or a plurality of filters which remove substantially all light below 480 nm and pass light in the wavelength range from 480 nm to 680 nm, such that the detection means is able to detect fluorescent light from said skin within the 500–580 nm wavelength range (yellow/green fluorescence) and within the 580–680 nm wavelength range (orange/red fluorescence).

4. The method of claim 3 wherein the detection means is selected from the group consisting of human eyes, a film emulsion camera, and a CCD camera.

* * * * *